United States Patent
Awasaguchi

(10) Patent No.: US 9,682,964 B2
(45) Date of Patent: Jun. 20, 2017

(54) AMIDE COMPOUND

(71) Applicant: Sumitomo Chemical Company, Limited, Tokyo (JP)

(72) Inventor: Kenichiro Awasaguchi, Takarazuka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 15/300,067

(22) PCT Filed: Mar. 17, 2015

(86) PCT No.: PCT/JP2015/058647
§ 371 (c)(1),
(2) Date: Sep. 28, 2016

(87) PCT Pub. No.: WO2015/151890
PCT Pub. Date: Oct. 8, 2015

(65) Prior Publication Data
US 2017/0144995 A1 May 25, 2017

(30) Foreign Application Priority Data

Apr. 1, 2014 (JP) ................................ 2014-075157

(51) Int. Cl.
| | | |
|---|---|---|
| *C07D 405/12* | (2006.01) | |
| *A01N 25/06* | (2006.01) | |
| *A01N 25/12* | (2006.01) | |
| *A01N 25/14* | (2006.01) | |
| *A01N 25/20* | (2006.01) | |
| *A01N 43/40* | (2006.01) | |
| *A01N 25/34* | (2006.01) | |

(52) U.S. Cl.
CPC ........... *C07D 405/12* (2013.01); *A01N 25/06* (2013.01); *A01N 25/12* (2013.01); *A01N 25/14* (2013.01); *A01N 25/20* (2013.01); *A01N 25/34* (2013.01); *A01N 43/40* (2013.01)

(58) Field of Classification Search
None
See application file for complete search history.

(56) References Cited

FOREIGN PATENT DOCUMENTS

| | | | | |
|---|---|---|---|---|
| JP | 2016011276 A | 1/2016 | | |
| WO | 2013003505 A1 | 1/2013 | | |
| WO | WO 2013003505 A1 * | 1/2013 | ........... | C07D 213/18 |
| WO | 2014054425 A1 | 4/2014 | | |
| WO | 2014119696 A1 | 8/2014 | | |
| WO | 2014168052 A1 | 10/2014 | | |

OTHER PUBLICATIONS

Int'l Search Report issued Apr. 14, 2015 in Int'l Application No. PCT/JP2015/058647 (English Translation).
Int'l Preliminary Report on Patentability issued Oct. 4, 2016 in Int'l Application No. PCT/JP2015/058647 (English Translation).

* cited by examiner

*Primary Examiner* — Nyeemah A Grazier
(74) *Attorney, Agent, or Firm* — Panitch Schwarze Belisaio & Nadel LLP

(57) ABSTRACT

A method is provided for producing an amide compound having an excellent control effect on arthropod pests. The method includes an arthropod pest control agent that contains the compound, and a step of applying an effective amount of the compound to control the arthropod pest or an arthropod pest-infested area.

6 Claims, No Drawings

AMIDE COMPOUND

CROSS-REFERENCE TO RELATED APPLICATION

This application is a Section 371 of International Application No. PCT/JP2015/058647, filed Mar. 17, 2015, which was published in the Japanese language on Oct. 8, 2015 under International Publication No. WO2015/151890 A1, and the disclosure of which is incorporated herein by reference.

BACKGROUND OF THE INVENTION

Field of the Invention

The present invention relates to an amide compound and a use thereof for arthropod pest control.

Description of the Related Art

WO2013/003505 describes that a certain kind of an amide compound can be used for control of ectoparasites.

An object of the present invention is to provide a compound having an excellent control effect on arthropod pests.

SUMMARY OF THE INVENTION

As a result of an intensive study to find a compound having an excellent controlling effect on arthropod pests, the present inventors have found that an amide compound represented by the following formula (I) (hereinbelow, sometimes referred to as the compound of the present invention) has an excellent controlling effect on arthropod pests, and thereby reaching the present invention.

More specifically, the present invention is as described below.

[1] An amide compound represented by formula (I), (I) [structure]

wherein
R$^1$ represents a hydrogen atom or a halogen atom,
m represents 1 or 2, and
n represents 0 or 1.

[2] The amide compound according to [1], wherein R$^1$ is a hydrogen atom or a fluorine atom.
[3] An arthropod pest control agent comprising the amide compound as defined in [1] or [2], and an inert carrier.
[4] A method for controlling arthropod pests comprising a step of applying an effective amount of the amide compound as defined in [1] or [2] to an arthropod pest or an arthropod pest-infested area.

DETAILED DESCRIPTION OF THE PREFERRED EMBODIMENTS

The compound of the present invention has an isomer derived from an asymmetric carbon atom, and the present invention contains each isomer having an arthropod pest control activity and an isomer mixture in an arbitrary ratio.

Examples of the "halogen atom" in this invention include a fluorine atom, a chlorine atom, a bromine atom, and an iodine atom.

Examples of the embodiments of the compound of the present invention include the following compounds.

(I) [structure]

In the formula (I), compounds wherein m is 1 and n is 0.
In the formula (I), compounds wherein m is 1 and n is 1.
In the formula (I), compounds wherein m is 2 and n is 0.
In the formula (I), compounds wherein R$^1$ is a hydrogen atom, and m is 1;
In the formula (I), compounds wherein R$^1$ is a hydrogen atom, and m is 2;
In the formula (I), compounds wherein R$^1$ is a halogen atom, and m is 1;
In the formula (I), compounds wherein R$^1$ is a fluorine atom, and m is 1;
In the formula (I), compounds wherein R$^1$ is a hydrogen atom, and n is 0;
In the formula (I), compounds wherein R$^1$ is a hydrogen atom, and n is 1;

Next, the method for producing the compound of the present invention will be described.

The compound of the present invention can be produced, for example, according to the following (Production Method 1) or (Production Method 2).

(Production Method 1)

The compound of the present invention can be produced by reacting a compound represented by formula (1) with a compound represented by formula (2), in the presence of a base.

[reaction scheme with (1), (2), and (I)]

wherein L represents a chlorine atom, a bromine atom or an iodine atom, R$^1$ represents a hydrogen atom or a halogen atom, m represents 1 or 2, and n represents 0 or 1.

The reaction is carried out in the presence of a base, usually in the presence of a solvent.

Examples of the base used in the reaction include inorganic bases such as sodium hydroxide, potassium hydroxide, sodium carbonate and potassium carbonate, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4dimethylaminopyridine.

Examples of the solvent used in the reaction include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile and butyronitrile, acid amides such as N,N-dimethylformamide, sulfoxides such as dimethyl sulfoxide, water, and mixtures thereof.

The reaction time is usually the range of 5 minutes to 72 hours.

The reaction temperature is usually in the range of –20 to 100° C.

The molar ratio of the compound represented by the formula (1) to the compound represented by the formula (2) used can be arbitrarily set, and is preferably equimolar or a ratio close thereto, and specifically, the compound represented by the formula (2) is at a ratio of 0.5 to 3 mol, based on 1 mol of the compound represented by the formula (1).

The base is usually used at an arbitrary ratio from 1 mol to an excess amount, and preferably at ratio of 1 to 3 mol, based on 1 mol of the compound represented by the formula (1).

After completion of the reaction, the reaction mixture is added to water, then extracted with an organic solvent, and subjected to usual post-treatment operations such as concentration, whereby the compound of the present invention can be isolated. Also, the isolated compound of the present invention also can be purified by operations such as chromatography, recrystallization and distillation.

(Production Method 2)

The compound of the present invention can be produced by reacting a compound represented by formula (3) with the compound represented by the formula (2), in the presence of a condensing agent.

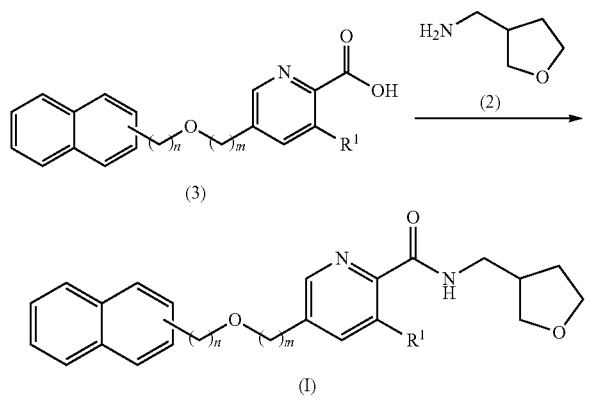

wherein $R^1$ represents a hydrogen atom or a halogen atom, m represents 1 or 2, and n represents 0 or 1.

The reaction is carried out in a solvent, usually in the presence of a condensing agent, and in the presence of a base as necessary.

Examples of the condensing agent used in the reaction include dicyclohexylcarbodiimide, 1-ethyl-3-(3-dimethylaminopropyl) carbodiimide hydrochloride, and benzotriazol-1-yloxytris (dimethylamino)phosphonium hexafluorophosphate.

Examples of the base used in the reaction include alkali metal hydroxides such as sodium hydroxide and potassium hydroxide, carbonates such as sodium carbonate and potassium carbonate, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

Examples of the solvent used in the reaction include aromatic hydrocarbons such as benzene and toluene, hydrocarbons such as hexane, ethers such as diethyl ether and tetrahydrofuran, halogenated hydrocarbons such as dichloromethane, 1,2-dichloroethane and chlorobenzene, acid amides such as N,N-dimethylformamide, esthers such as ethyl acetate and butyl acetate, and mixtures thereof.

The reaction is carried out, further in the presence of 1-hydroxybenzotriazole, 1-hydroxy-7-azabenzotriazole, N-hydroxysuccinimide or the like, usually at an arbitrary ratio from 0.01 to 1 mol, and preferably at a ratio of 0.05 to 0.2 mol, based on 1 mol of the compound represented by the formula (3), as necessary.

The reaction time is usually in the range of 5 minutes to 72 hours.

The reaction temperature is usually in the range of –20° C. to 100° C. (–20° C. to the boiling point of the solvent when the boiling point of the used solvent is less than 100° C.).

The molar ratio of the compound represented by the formula (3) to the compound represented by the formula (2) used can be arbitrarily set, and is preferably equimolar or a ratio close thereto, and for example, the compound represented by the formula (2) is at a ratio of 1 to 3 mol, based on 1 mol of the compound represented by the formula (3).

The condensing agent is usually used in an arbitrary ratio from 1 mol to an excess amount, and preferably at a ratio of 1 to 3 mol, based on 1 mol of the compound represented by the formula (3).

The base is usually used at an arbitrary ratio from 1 mol to an excess amount, and preferably at a ratio of 1 to 3 mol, based on 1 mol of the compound represented by the formula (3).

After completion of the reaction, the reaction mixture is added to water, then extracted with an organic solvent, and subjected to usual post-treatment operations such as concentration, whereby the compound of the present invention can be isolated. Also, the isolated compound of the present invention also can be purified by operations such as chromatography, recrystallization and distillation.

Next, the method for producing an intermediate used in the production of the compound of the present invention will be described.

(Reference Production Method 1)

The compound represented by the formula (1) can be produced by reacting a compound represented by formula (4) with a halogenating agent.

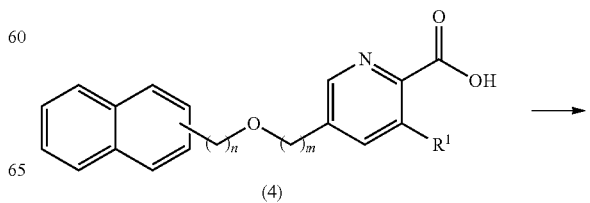

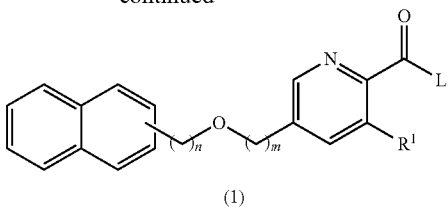

(1)

wherein L represents a chlorine atom, a bromine atom or an iodine atom, $R^1$ represents a hydrogen atom or a halogen atom, m represents 1 or 2, and n represents 0 or 1.

The reaction is carried out, in the presence of a solvent, usually in an inert gas atmosphere such as nitrogen.

Examples of the halogenating agent used in the reaction include thionyl chloride, oxalyl chloride and phosphorus oxychloride.

Examples of the solvent used in the reaction include esters such as methyl acetate and ethyl acetate, ethers such as 1,4-dioxane, tetrahydrofuran, ethylene glycol dimethyl ether and tert-butyl methyl ether, aliphatic hydrocarbons such as hexane and heptane, aromatic hydrocarbons such as toluene and xylene, halogenated hydrocarbons such as chlorobenzene, and mixtures thereof.

The reaction time is usually in the range of 5 minutes to 24 hours.

The reaction temperature is usually in the range of 0° C. to 100° C.

The halogenating agent is usually used in an arbitrary ratio from 1 mol to an excess amount, and preferably at a ratio of 1 to 5 mol, based on 1 mol of the compound represented by the formula (4).

The reaction is carried out, further in the presence of 0.001 to 0.5 mol and preferably 0.01 to 0.1 mol of N,N-dimethylformamide, based on 1 mol of the compound represented by the formula (4), as necessary.

After completion of the reaction, the reaction mixture is subjected to post-treatment operations such as direct concentration, whereby the compound represented by the formula (1) can be isolated. The isolated compound represented by the formula (1) is usually used for the reaction in the next step without purification, but can be purified by distillation or the like as necessary.

(Reference Production Method 2)

The compound represented by the formula (4) can be produced by subjecting a compound represented by formula (5) to a hydrolysis reaction, in the presence of a base.

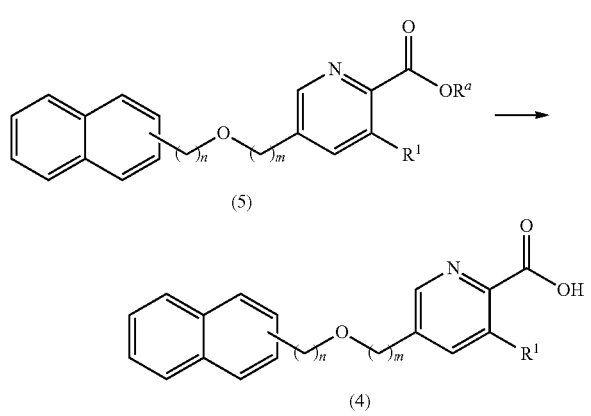

wherein $R^3$ represents a methyl group or an ethyl group, $R^1$ represents a hydrogen atom or a halogen atom, m represents 1 or 2, and n represents 0 or 1.

The reaction is carried out in the presence of a base, and in the presence of water and an organic solvent.

Examples of the base used in the reaction include alkali metal hydroxides such as lithium hydroxide, sodium hydroxide and potassium hydroxide, and alkali metal alkoxides such as potassium-tert-butoxide.

Examples of the solvent used in the reaction include ethers such as 1,4-dioxane, tetrahydrofuran, ethylene glycol dimethyl ether and tert-butyl methyl ether, aromatic hydrocarbons such as toluene and xylene, halogenated hydrocarbons such as chlorobenzene, nitriles such as acetonitrile and butyronitrile, alcohols such as methanol, ethanol and propanol, and mixtures thereof.

The reaction time is usually in the range of 5 minutes to 72 hours.

The reaction temperature is usually in the range of 0° C. to 100° C.

The base is usually used at an arbitrary ratio from 1 mol to an excess amount, and preferably at a ratio of 1 to 5 mol, based on 1 mol of the compound represented by the formula (5).

After completion of the reaction, the reaction mixture is neutralized by an acidic aqueous solution such as hydrochloric acid and extracted with an organic solvent, then the organic layer is subjected to post-treatment operations such as drying and concentration, whereby the compound represented by the formula (4) can be isolated. The isolated compound represented by the formula (4) can be further purified by chromatography, recrystallization, distillation and the like, but also can be directly used for the next step.

(Reference Production Method 3)

The compound represented by the formula (5) can be produced by reacting a compound represented by formula (6) with a compound represented by formula (7), in the presence of a base.

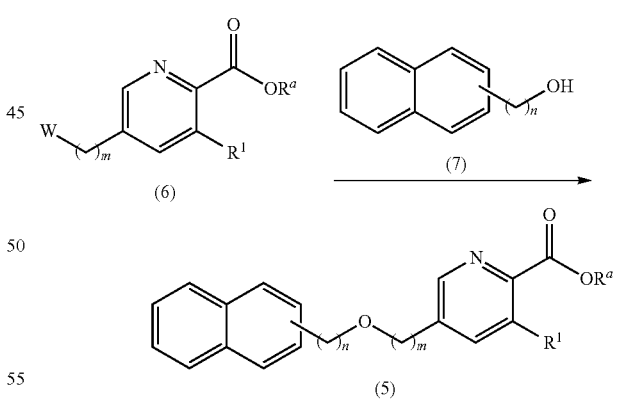

wherein $R^3$ represents a methyl group or an ethyl group, W represents a leaving group (for example, chlorine, bromine, iodine, a methanesulfonyloxy group, a trifluoromethanesulfonyloxy group, a p-toluenesulfonyloxy group, etc.), $R^1$ represents a hydrogen atom or a halogen atom, m represents 1 or 2, and n represents 0 or 1.

The reaction is carried out in a solvent, in the presence of a base, usually in an inert gas atmosphere such as nitrogen.

Examples of the base used in the reaction include alkali metals such as sodium and potassium, alkyllithiums such as n-butyllithium, metal hydride compounds such as sodium hydride and potassium hydride, carbonates such as sodium carbonate and potassium carbonate, alkali metal alkoxides such as potassium-tert-butoxide, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

Examples of the solvent used in the reaction include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile and butyronitrile, acid amides such as N,N-dimethylformamide, sulfoxides such as dimethyl sulfoxide, and mixtures thereof.

The reaction time is usually in the range of 5 minutes to 72 hours.

The reaction temperature is usually in the range of −40 to 100° C.

The molar ratio of the compound represented by the formula (6) to the compound represented by the formula (7) used can be arbitrarily set, and is preferably equimolar or a ratio close thereto, and specifically, the compound represented by the formula (7) is at a ratio of 0.5 to 3 mol, based on 1 mol of the compound represented by the formula (6).

The base is usually used at an arbitrary ratio from 1 mol to an excess amount, and preferably at a ratio of 1 to 3 mol, based on 1 mol of the compound represented by the formula (6).

After completion of the reaction, the reaction mixture is added to water, then extracted with an organic solvent, and subjected to usual post-treatment operations such as concentration, whereby the compound represented by the formula (5) can be isolated. Also, the isolated compound represented by the formula (5) also can be purified by operations such as chromatography, recrystallization and distillation.

(Reference Production Method 4)

A compound represented by formula (5-a) can be produced by subjecting a compound represented by formula (8) and a compound represented by formula (7-a) to Mitsunobu reaction.

The reaction is carried out in a solvent, in the presence of a Mitsunobu reagent and a phosphine compound, usually in an inert gas atmosphere such as nitrogen.

The Mitsunobu reagent used in the reaction includes azo Mitsunobu reagents such as diethyl azodicarboxylate (DEAD), diisopropyl azodicarboxylate (DIAD), N,N,N',N'-tetraisopropyl azodicarboxamide (TIPA), N,N,N',N'-tetramethyl azodicarboxamide (TMAD), 1,1'-(azodicarbonyl)dipiperidine (ADDP) and 1,6-dimethyl-1,5,7-hexahydro-1,4,6,7,-tetrazocin-2,5-dione (DHTD), phosphorane Mitsunobu reagents such as (cyanomethylene)tributylphosphorane (CMBP) and (cyanomethylene)trimethylphosphorane, and the like.

Examples of the phosphine compound used in the reaction include triarylphosphines such as triphenylphosphine, trialkylphosphines such as tributylphosphine, and the like.

Examples of the solvent used in the reaction include aromatic hydrocarbons such as benzene and toluene, hydrocarbons such as hexane, ethers such as diethyl ether, tetrahydrofuran and 1,4-dioxane, halogenated hydrocarbons such as chloroform, dichloromethane, 1,2-dichloroethane and chlorobenzene, acid amides such as N,N-dimethylformamide, esters such as ethyl acetate and butyl acetate, and mixtures thereof.

The reaction time of the reaction is usually in the range of 5 minutes to 72 hours.

The reaction temperature of the reaction is usually in the range of −10° C. to 80° C.

The Mitsunobu reagent used in the reaction is usually used at an arbitrary ratio from 1 mol to an excess amount, and preferably at a ratio of 1 to 3 mol, based on 1 mol of the compound represented by the formula (8).

The phosphine compound used in the reaction is usually used at an arbitrary ratio from 1 mol to an excess amount, and preferably at a ratio of 1 to 3 mol, based on 1 mol of the compound represented by the formula (8).

After completion of the reaction, the reaction mixture is added to water, then extracted with an organic solvent, and subjected to usual post-treatment operations such as concentration, whereby the compound of the present invention can be isolated. Also, the isolated compound of the present invention also can be purified by operations such as chromatography, recrystallization and distillation.

(Reference Production Method 5)

A compound represented by a formula (6-a) can be produced by reacting the compound represented by the formula (8) with a sulfonylating agent, in the presence of a base.

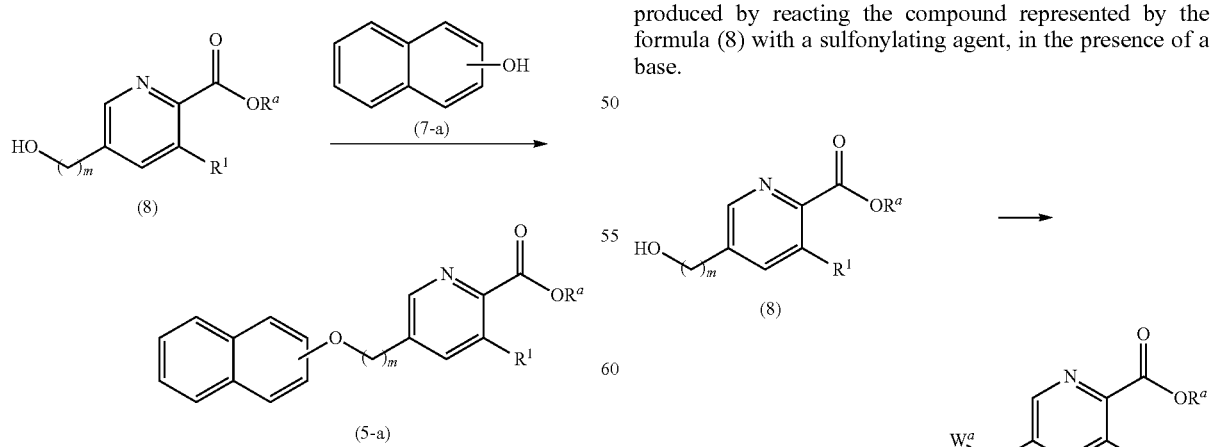

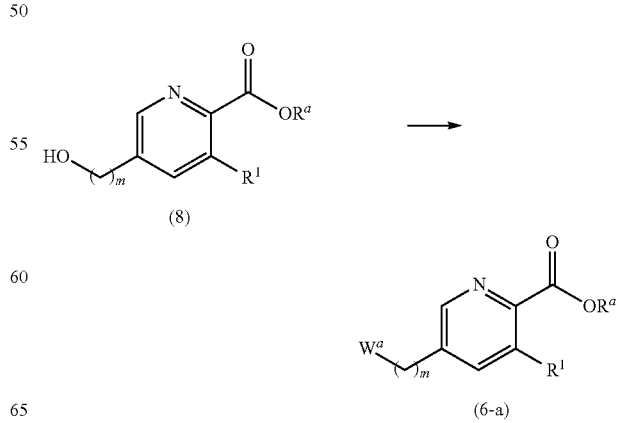

wherein $R^3$ represents a methyl group or an ethyl group, $R^1$ represents a hydrogen atom or a halogen atom, m represents 1 or 2, and n represents 0 or 1.

wherein $R^3$ represents a methyl group or an ethyl group, $W^b$ represents a leaving group (for example, a methanesulfonyloxy group, a trifluoromethanesulfonyloxy group, a p-toluenesulfonyloxy group, etc.), $R^1$ represents a hydrogen atom or a halogen atom, m represents 1 or 2, and n represents 0 or 1.

The reaction is carried out in a solvent, in the presence of a base, usually in an inert gas atmosphere such as nitrogen.

Examples of the sulfonylating agent used in the reaction include methanesulfonyl chloride, trifluoromethanesulfonyl chloride, p-toluenesulfonyl chloride, trifluoromethanesulfonic anhydride, and the like.

Examples of the base used in the reaction include carbonates such as sodium carbonate and potassium carbonate, alkali metal alkoxides such as potassium-tert-butoxide, tertiary amines such as triethylamine, diisopropylethylamine, 1,8-diazabicyclo[5.4.0]undec-7-ene and 1,5-diazabicyclo[4.3.0]non-5-ene, and nitrogen-containing aromatic compounds such as pyridine and 4-dimethylaminopyridine.

Examples of the solvent used in the reaction include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile and butyronitrile, acid amides such as N,N-dimethylformamide, sulfoxides such as dimethyl sulfoxide, and mixtures thereof.

The reaction time is usually in the range of 5 minutes to 72 hours.

The reaction temperature is usually in the range of −40 to 100° C.

The sulfonylating agent is usually used in an arbitrary ratio from 1 mol to an excess amount, and preferably at a ratio of 1 to 3 mol, based on 1 mol of the compound represented by the formula (8).

The base is usually used at an arbitrary ratio from 1 mol to an excess amount, and preferably at a ratio of 1 to 3 mol, based on 1 mol of the compound represented by the formula (8).

After completion of the reaction, the reaction mixture is added to water, then extracted with an organic solvent, and subjected to usual post-treatment operations such as concentration, whereby the compound represented by the formula (6-a) can be isolated. Also, the isolated compound represented by the formula (6-a) also can be purified by operations such as chromatography, recrystallization and distillation.

(Reference Production Method 6)

A compound represented by formula (6-b) can be produced by subjecting the compound represented by the formula (8) to a halogenation reaction.

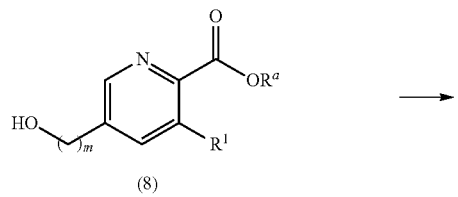

(8)

⟶

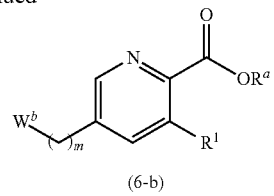

(6-b)

wherein $R^3$ represents a methyl group or an ethyl group, $W^b$ represents a leaving group (for example, chlorine, bromine, iodine, etc.), $R^1$ represents a hydrogen atom or a halogen atom, m represents 1 or 2, and n represents 0 or 1.

Examples of the halogenation reaction include (1) Method using thionyl chloride, phosphorous oxychloride, or the like, and (2) Method using a halogenating agent, in the presence of phosphine.

As an example, the method using a halogenating agent, in the presence of phosphine will be specifically described.

The reaction is carried out in a solvent, in the presence of phosphine, in the presence of a base as necessary, and usually in an inert gas atmosphere such as nitrogen.

Examples of the halogenating agent used in the reaction include iodine, carbon tetrabromide, carbon tetrachloride and the like.

Examples of the phosphine used in the reaction include tributylphosphine, triphenylphosphine, and the like.

Examples of the base used in the reaction include tertiary amines such as triethylamine and diisopropylethylamine, 1,8-diazabicyclo[5.4.0]undec-7-ene and 1,5-diazabicyclo[4.3.0]non-5-ene, and nitrogen-containing aromatic compounds such as imidazole, pyridine and 4-dimethylaminopyridine.

Examples of the solvent used in the reaction include ethers such as 1,4-dioxane, tetrahydrofuran, ethylene glycol dimethyl ether and tert-butyl methyl ether, aliphatic hydrcarbons such as hexane, heptane and octane, aromatic hydrocarbons such as toluene and xylene, halogenated hydrocarbons such as dichloromethane, chloroform and chlorobenzene, esters such as ethyl acetate and butyl acetate, nitriles such as acetonitrile and butyronitrile, and mixtures thereof.

The reaction time is usually in the range of 5 minutes to 72 hours.

The reaction temperature is usually in the range of −20 to 100° C.

The halogenating agent is usually used in an arbitrary ratio from 1 mol to an excess amount, and preferably at a ratio of 1 to 5 mol, based on 1 mol of the compound represented by the formula (8).

The base used as necessary is usually used at an arbitrary ratio from 0.01 mol to an excess amount, and preferably at a ratio of 1 to 5 mol, based on 1 mol of the compound represented by the formula (8).

After completion of the reaction, the reaction mixture is added to water, then extracted with an organic solvent, and subjected to usual post-treatment operations such as concentration, whereby the compound represented by the formula (6-b) can be isolated. Also, the isolated compound represented by the formula (6-b) also can be purified by operations such as chromatography, recrystallization and distillation.

(Reference Production Method 7)

The compound represented by the formula (6-b) can be produced by reacting a compound represented by formula (9) with a halogenating agent, in the presence of a radical initiator.

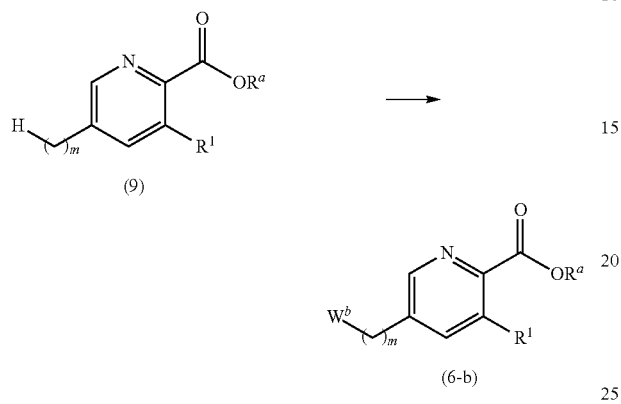

wherein $R^3$ represents a methyl group or an ethyl group, $W^b$ represents a leaving group (for example, a chlorine atom, a bromine atom, an iodine atom, etc.), $R^1$ represents a hydrogen atom or a halogen atom, m represents 1 or 2, and n represents 0 or 1.

The reaction is carried out in a solvent, in the presence of a radical initiator, usually in an inert gas atmosphere such as nitrogen.

Examples of the halogenating agent used in the reaction include bromine, iodine, N-chlorosuccinimide, N-bromosuccinimide, N-iodosuccinimide, and the like.

Examples of the radical initiator used in the reaction include benzoyl peroxide, azobisisobutyronitrile, tert-butyl peroxide, and the like.

Examples of the solvent used in the reaction include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as benzene, halogenated hydrocarbons such as chlorobenzene, nitriles such as acetonitrile and butyronitrile, and mixtures thereof.

The reaction time is usually in the range of 5 minutes to 72 hours.

The reaction temperature is usually in the range of 0 to 100°.

The halogenating agent is usually used in an arbitrary ratio from 1 mol to an excess amount, and preferably at a ratio of 1 to 5 mol, based on 1 mol of the compound represented by the formula (9).

The radical initiator is usually used in an arbitrary ratio from 0.01 mol to an excess amount, and preferably at a ratio of 0.1 to 1 mol, based on 1 mol of the compound represented by the formula (9).

After completion of the reaction, the reaction mixture is added to water, then extracted with an organic solvent, and subjected to usual post-treatment operations such as concentration, whereby the compound represented by the formula (6-b) can be isolated. Also, the isolated compound represented by the formula (6-b) also can be purified by operations such as chromatography, re-crystallization and distillation.

(Reference Production Method 8)

The compound represented by the formula (4) can be produced by reacting a compound represented by formula (10) with a base and then reacting the reactant with dry ice (carbon dioxide).

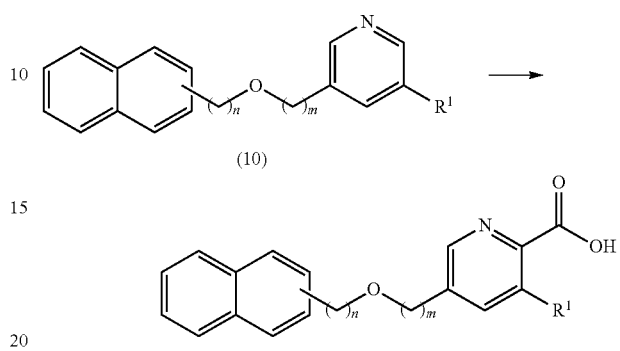

wherein $R^1$ represents a hydrogen atom or a halogen atom, m represents 1 or 2, and n represents 0 or 1.

The reaction is carried out in a solvent, usually in the presence of a base, usually in an inert gas atmosphere such as nitrogen, and further the treatment with dry ice is carried out.

The base used in the reaction includes organic lithium compounds such as n-butyllithium, sec-butyllithium, tert-butyllithium and 2,4,6-trimethylphenyllithium, lithium diisopropylamide, lithium hexamethyldisilazide, and the like.

Examples of the solvent used in the reaction include aromatic hydrocarbons such as benzene and toluene, hydrocarbons such as hexane, ethers such as diethyl ether and tetrahydrofuran, and mixtures thereof.

The reaction time of the reaction is usually in the range of 5 minutes to 72 hours.

The reaction temperature of the reaction is usually in the range of −100° C. to 40° C.

The base used in the reaction is usually used at an arbitrary ratio from 1 mol to an excess amount, and preferably at a ratio of 1 to 3 mol, based on 1 mol of the compound represented by the formula (10).

The dry ice used in the reaction is usually used at an arbitrary ratio from 1 mol to an excess amount, based on 1 mol of the compound represented by the formula (10).

After completion of the reaction, the reaction mixture is added to water and washed with an organic solvent, then the aqueous layer is neutralized by an acidic aqueous solution such as hydrochloric acid and extracted with an organic solvent, and subjected to post-treatment operations such as concentration, whereby the compound represented by the formula (4) can be obtained. Also, the obtained compound represented by the formula (4) is usually used for the reaction in the next step without purification, but also can be purified by operations such as chromatography and recrystallization as necessary.

(Reference Production Method 9)

The compound represented by the formula (10) can be produced by reacting a compound represented by formula (11) with the compound represented by the formula (7), in the presence of a base.

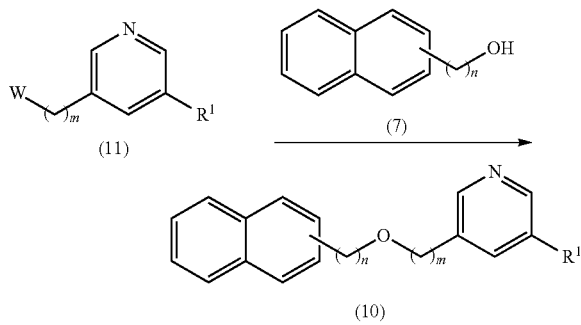

wherein W represents a leaving group (for example, chlorine, bromine, iodine, a methanesulfonyloxy group, a trifluoromethanesulfonyloxy group, a p-toluenesulfonyloxy group, etc.), $R^1$ represents a hydrogen atom or a halogen atom, m represents 1 or 2, and n represents 0 or 1.

The reaction is carried out in a solvent, in the presence of a base, usually in an inert gas atmosphere such as nitrogen.

Examples of the base used in the reaction include alkali metals such as sodium and potassium, alkyllithiums such as n-butyllithium, metal hydride compounds such as sodium hydride and potassium hydride, carbonates such as sodium carbonate and potassium carbonate, alkali metal alkoxides such as potassium-tert-butoxide, tertiary amines such as triethylamine, diisopropylethylamine, 1,8-diazabicyclo[5.4.0]undec-7-ene and 1,5-diazabicyclo[4.3.0]non-5ene, and nitrogen-containing aromatic compounds such as pyridine and 4-dimethylaminopyridine.

Examples of the solvent used in the reaction include ethers such as 1,4-dioxane, tetrahydrofuran, ethylene glycol dimethyl ether and tert-butyl methyl ether, aliphatic hydrocarbons such as hexane, heptane and octane, aromatic hydrocarbons such as toluene and xylene, halogenated hydrocarbons such as chlorobenzene, esters such as ethyl acetate and butyl acetate, nitriles such as acetonitrile and butyronitrile, acid amides such as N,N-dimethylformamide, sulfoxides such as dimethyl sulfoxide, and mixtures thereof.

The reaction time is usually in the range of 5 minutes to 72 hours.

The reaction temperature is usually in the range of −40 to 100° C.

The molar ratio of the compound represented by the formula (11) to the compound represented by the formula (7) used can be arbitrarily set, and is preferably equimolar or a ratio close thereto, and specifically, the compound represented by the formula (7) is at a ratio of 0.5 to 3 mol, based on 1 mol of the compound represented by the formula (11).

The base is usually used at an arbitrary ratio from 1 mol to an excess amount, and preferably at a ratio of 1 to 3 mol, based on 1 mol of the compound represented by the formula (11).

After completion of the reaction, the reaction mixture is added to water, then extracted with an organic solvent, and subjected to usual post-treatment operations such as concentration, whereby the compound represented by the formula (10) can be isolated. Also, the isolated compound represented by the formula (10) also can be purified by operations such as chromatography, recrystallization and distillation.

The arthropod pest on which the composition of the present invention has a control effect includes pest insects and pest mites. More specifically, examples include those shown below. Hemiptera pests: *Delphacidae* such as *Laodelphax striatellus, Nilaparvata lugens,* and *Sogatella furcifera, Deltocephalidae* such as *Nephotettix cincticeps* and *Nephotettix virescens, Aphididae* such as *Aphis gossypii* and *Myzus persicae, Pentatomidae* such as *Nezara antennata, Riptortus clavetus, Eysarcoris lewisi, Eysarcoris parvus, Plautia stali, Halyomorpha mista, Stenotus rubrovittatus,* and *Trigonotylus ruficornis, Aleyrodidae* such as *Trialeurodes vaporariorum* and *Bemisia argentifolii, Coccidae* such as *Aonidiella aurantii, Comstockaspis perniciosa, Unaspis citri, Ceroplastes rubens,* and *Icerya purchasi, Tingidae, Cimicoidea* such as *Cimex lectularius, Psyliidae,* etc.;

Lepidoptera pests: *Pyralidae* such as *Chilo suppressalis Cnaphalocrocis medinalis, Notarcha derogata,* and *Plodia interpunctella, Noctuidae* such as *Spodoptera litura, Pseudaletia separata, Tricoplusia* spp., *Heliothis* spp., and *Helicoverpa* spp., *Pieridae* such as *Pieris rapae, Adoxophyes* spp., *Tortricidae* such as *Grapholita molesta* and *Cydia pomonella, Carposinidae* such as *Carposina niponensis, Lyonetiidae* such as *Lyonetia* spp., *Lymantriidae* such as *Lymantria* spp. and *Euproctis* spp., *Yponomeutidae* such as *Plutella xylostella, Gelechiidae* such as *Pectinophora gossypiella, Arctiidae* such as *Hyphantria cunea, Tineidae* such as *Tinea translucens* and *Tineola bisselliella,* etc.;

Diptera pests: *Culex* such as *Culex pipiens pallens, Culex tritaeniorhynchus,* and *Culex quinquefasciatus, Aedes* spp. such as *Aedes aegypti* and *Aedes albopictus, Anopheles* spp. such as *Anopheles sinensis, Chironomidae, Mascidae* such as *Musca domestica* and *Muscina stabulans, Calliphoridae, Sarcophagidae, Fanniidae, Anthomyiidae* such as *Delia platura* and *Delia antiqua, Agromyzidae* such as *Liriomyza trifolii, Tephritidae, Drosophilidae, Phoridae* such as *Megaselia spiracularis, Psychodidae* such as *Clogmia albipunctata, Simuliidae, Tabanidae, Stomoxyidae,* etc., Coleoptera pests: *Diabrotica* such as *Diabrotica virgifera virgifera* and *Diabrotica undecimpunctata howardi, Scarabaeidae* such as *Anomala cuprea* and *Anomala rufocuprea, Curculionidae* such as *Sitophilus zeamais, Lissorhoptrus oryzophilus,* and *Callosobruchuys chienensis, Tenebrionidae* such as *Tenebrio molitor* and *Tribolium castaneum, Chrysomelidae* such as *Oulema oryzae, Aulacophora femoralis, Phyllotreta striolata,* and *Leptinotarsa decemlineata, Dermestidae* such as *Dermestes maculates, Anobiidae, Epilachna* such as *Epilachna vigintioctopunctata, Lyctidae, Bostrychidae, Ptinidae, Cerambycidae,* and *Paederus fuscipes,* etc.;

Blattidea pests: *Blattella germanica, Periplaneta fuliginosa, Periplaneta americana, Periplaneta brunnea, Blatta orientalis,* etc.;

Thysanoptera pests: *Thrips palmi, Thrips tabaci, Frankliniella occidentalis, Frankliniella intonsa,* etc.;

Hymenoptera pests: *Formicidae* such as *Monomorium pharaosis, Formica fusca japonica, Ochetellus glaber, Pristomyrmex pungens,* and *Pheidole noda, Vespidae, Bethylidae, Tenthredinidae* such as *Athalia japonica,* etc.;

Orthoptera pests: *Gryllotalpidae, Acrididae, Gryllidae,* etc.;

Aphaniptera pests: *Ctenocephalides felis, Ctenocephalides canis, Pulex irritans, Xenopsylla cheopis,* etc.

Anoplura pests: *Pediculus humanus corporis, Phthirus pubis, Haematopinus eurysternus, Dalmalinia ovis, Haematopinus suis,* etc.;

Isoptera pests: Subterranean termites such as *Recticulitermes speratus, Coptotermes formosanus, Reticulitermes flavipes, Reticulitermes hesperus, Reticulitermes virginicus, Reticulitermes tibialis,* and *Heterotermes aureus,* Drywood termites such as *Incisitermes minor,* Dampwood termites such as *Zootermopsis nevadensis,* etc.;

Acarina pests: *Tetranychidae* such as *Tetranychus urticae, Tetranychus kanzawai, Panonychus citri, Panonychus ulmi,* and *Oligonychus* spp., *Eriophyidae* such as *Aculops lycopers, Aculops pelekasai,* and *Aculus schlechtendali, Tarsonemidae* such as *Polyphagotarsonemus latus, Tenuipalpidae, Tuckerellidae, Metastigmata* such as *Haemaphysalis longicornis, Haemaphysalis flava, Dermacentor variabilis, Haemaphysalis flava, Dermacentor taiwanicus, Ixodes ovatus, Ixodes persulcatus, Ixodes scapularis, Boophilus microplus, Amblyomma americanum,* and *Rhipicephalus sanguineus, Acaridae* such as *Tyrophagus putrescentiae, Pyroglyphidae* such as *Dermatophagoides farinae* and *Dermatophagoides ptrenyssnus, Cheyletidae* such as *Cheyletus eruditus, Cheyletus malaccensis,* and *Cheyletus moorei, Dermanyssidae* such as *Ornithonyssus bacoti, Ornithonyssus sylvairum,* and *Dermanyssus gallinae, Trombiculidae* such as *Leptotrombidium akamushi,* etc.;

Arachnida: *Chiracanthium japonicum, Latrodectus hasseltii,* etc.;

Chilopoda: *Thereuonema hilgendorfi, Scolopendra subspinipes,* etc.;

Diplopoda: *Oxidus gracilis, Nedyopus tambanus,* etc.;

Isopoda: *Armadillidium vulgare,* etc.;

The arthropod pest control agent of the present invention contains the compound of the present invention and an inert carrier. In the present invention, an inert carrier refers to an extender, a diluent and the like used in epidemic prevention and in the agricultural field. The arthropod pest control agent of the present invention is usually obtained by mixing the compound of the present invention and an inert carrier such as a solid carrier, a liquid carrier or a gaseous carrier, and adding a surfactant or other auxiliaries for formulation as necessary, to be formulated into emulsifiable concentrates, oil formulations, dust formulations, granules, wettable powder, flowables, microcapsule formulations, aerosols, fumigants, poisonous baits, resin formulations, and the like. These formulations usually contain the compound of the present invention in an amount of 0.01 to 95% by weight.

Examples of the solid carrier which is used in the formulation include fine powder and granules of clays (kaolin clay, diatomaceous earth, bentonite, Fubasami clay, acid clay, etc.), synthetic hydrous silicon oxide, talc, ceramics, other inorganic minerals (sericite, quartz, sulfur, activated carbon, calcium carbonate, hydrated silica, etc.), fine powder and granulated substances of chemical fertilizers (ammonium sulfate, ammonium phosphate, ammonium nitrate, urea, ammonium chloride, etc.) and the like.

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc.).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkyl sulfonates, alkylbenzene sulfonates and alkylsulfates.

The other auxillaries for formulation include such as fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

The arthropod pest control agent of the present invention is applied to an arthropod pest directly and/or an arthropod pest-infested area, whereby the arthropod pest can be controlled.

The method for controlling arthropod pests of the present invention is carried out by applying an effective amount of the compound of the present invention to an arthropod pest or an arthropod pests-infested area. In the method for controlling arthropod pests of the present invention, the compound of the present invention is usually used in the form of the arthropod pest control agent of the present invention.

The arthropod pest-infested area includes rice fields, fields, orchards, non-agricultural lands, house, and the like.

The application can be carried out by the same application method as a conventional case, as long as the compound of the present invention can be contacted to or taken by an arthropod pest.

Examples of the application method include spray treatment, soil treatment, seed treatment and hydroponic liquid treatment.

When the arthropod pest control agent of the present invention is used in arthropod pest controlling in the agricultural field, the application amount is usually 1 to 10000 g per the amount of the compound of the present invention of 10000 $m^2$. When the arthropod pest control agent of the present invention is formulated into an emulsifiable concentrate, wettable powder, flowable or the like, the pest control agent is usually diluted with water for an application so as to have a concentration of the active ingredient of 0.01 to 10000 ppm, and dust formulations, granules and the like are usually applied as they are.

These formulations and formulation solutions diluted with water may be directly treated by being sprayed on an arthropod pest or a plant such as crops which should be protected from arthropod pests, and also may be treated on a soil in order to control an arthropod pest that infests in the soil of cultivated land.

Also, the resin formulation processed into a sheet or string can be also treated by a method such as winding it around crops, spreading it in the vicinity of crops, or spreading it to the soil around crop roots.

When the arthropod pest control agent of the present invention is used in controlling the arthropod pest that inhabits in the house, the application amount is usually 0.01 to 1000 mg in an amount of the compound of the present invention per 1 $m^2$ of an area to be treated, in the case of using it on a planar area, and is usually 0.01 to 500 mg in an amount of the compound of the present invention per 1 m³ of a space to be treated, in the case of using it in a space. When the arthropod pest control agent of the present invention is formulated into an emulsifiable concentrate, wettable powder, flowable or the like, the pest control agent is usually diluted with water for an application so as to have a concentration of the active ingredient of 0.1 to 1000 ppm, and oil formulations, aerosols, fumigants, poisonous baits and the like are applied as they are.

The compound of the present invention can be used in the farmland where the following crops are grown.

Crops: corn, rice, wheat, barley, rye, oat, sorghum, cotton, soybean, peanut, sarrazin, sugar beet, rapeseed, sunflower, sugar cane, tobacco, etc., Vegetables: Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc., Flower and ornamental plants, Ornamental foliage plants, Fruit trees: pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape persimmon, olive, loquat, banana, coffee, date, coconut, etc., Trees other than fruit trees: tea, mulberry, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), etc.

The crops also contains genetically modified crops.

The arthropod pest control agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide (1) Organic Phosphorus Compounds

Acephate, Aluminium phosphide, butathiofos, cadusafos, chlorethoxyfos, chlorfenvinphos, chlorpyrifos, chlorpyrifos-methyl, cyanophos: CYAP, diazinon, DCIP: dichlorodiisopropyl ether, dichlofenthion: ECP, dichlorvos: DDVP, dimthoate, dimethylvinphos, disulfoton, EPN, ethion, ethoprophos, etrimfos, fenthion: MPP, fenitrothion: MEP, fosthiazate, formothion, Hydrogen phosphide, isofenphos, isoxathion, malathion, mesulfenfos, methidathion: DMTP, monocrotophos, naled: BRP, oxydeprofos: ESP, parathion, phosalone, phosmet: PMP, pirimiphos-methyl, pyridafenthion, quinalphos, phenthoate: PAP, profenofos, propaphos, prothiofos, pyraclorfos, salithion, sulprofos, tebupirimfos, temephos, tetrachlorvinphos, terbufos, thiometon, trichlorphon: DEP, vamidothion, phorate, and cadusafos.

(2) Carbamate Compounds

Alanycarb, bendiocarb, benfuracarb, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, oxamyl, pirimicarb, propoxur: PHC, XMC, thiodicarb, xylylcarb, and aldicarb.

(3) Pyrethroid Compounds

Acrinathrin, allethrin, beta-cyfluthrin, bifenthrin, cycloprothrin, cyfluthrin, cyhalothrin, cypermethrin, deltamethrin, esfenvalerate, etofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro -4-(methoxymethyl)benzyl (EZ)-(1RS, 3RS, 1RS, 3SR)-2,2-dimethyl-3-prop-1-enylcyclopropanecarboxylate, 2,3,5,6-tetrafluoro-4-methylbenzyl (EZ)-1RS, 3RS; 1RS, 3SR)-2,2-dimethyl-3-prop-1-enylcyclopropanecarboxylate, and 2,3,5,6-tetrafluoro-4-(methoxymethyl) benzyl (1RS, 3RS; 1RS, 3SR)-2,2-dimethyl-3-(2-methyl-1-propenyl)cyclopropanecarboxylate.

(4) Nereistoxin Compounds

Cartap, bensultap, thiocyclam, monosultap, and bisultap.

(5) Neonicotinoid Compounds

Imidacloprid, nitenpyram, acetamiprid, thiamethoxam, thiacloprid, dinotefuran, and clothianidin.

(6) Benzoyl Urea Compounds

Chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole Compounds

Acetoprole, ethiprole, fipronil, vaniliprole, pyriprole, and pyrafluprole.

(8) Bt Toxins

Living spores derived from *Bacillus thuringiensis* and produced cyrstalline toxins and mixtures thereof;

(9) Hydrazine Compounds

Chromafenozide, halofenozide, methoxyfenozide, and tebufenozide.

(10) Organic Chlorine Compounds

Aldrin, dieldrin, dienochlor, endosulfan, and methoxychlor.

(11) Other Active Ingredients of Insecticide

Machine oil, nicotine-sulfate; avermectin-B, bromopropylate, buprofezin, chlorphenapyr, cyantraniliprole, cyromazine, D-D; 1,3-Dichloropropene, emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, and cyantraniliprole.

Active Ingredients of Miticide

Acequinocyl, amitraz, benoximate, bifenaate, bromopropylate, chinomethionat, chlorobenzilate, CPCBS: chlorfenson, clofentezine, cyflumetofen, kelthane: dicofol, etoxazole, fenbutatin oxide, fenothiocarb, fenpyroximate, fluacrypyrim, fluproxyfen, hexythiazox, propargite: BPPS, polynactins, pyridaben, Pyrimidifen, tebufenpyrad, tetradifon, spirodiclofen, spiromesifen, spirotetramat, amidoflumet, and cyenopyrafen.

DCIP, fosthiazate, levamisol, methyisothiocyanate, morantel tartarate, and imicyafos.

Active Ingredients of Fungicide

Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine fungicidal compounds such as fenpropimorph, tridemorph, and fenpropidin;

Benzimidazole fungicidal compounds such as carbendezim, benomyl, thiabendazole, and thiophanate-methyl;

procymidone; cyprodinil; pryrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil and tiadinil.

Active Ingredients of Plant Growth Regulator

Ethephon, chlormequat-chloride, mepiquat-chloride, Gibberellin A represented by Gibberellin A3, abscisic acid, Kinetin, benzyladenine, 1,3-diphenylurea, forchlorfenuron, thidiazuron, 4-oxo-4-(2-diphenylethyl)aminobutyric acid, methyl 5-(trifluoromethyl)benzo[b]thiophene-2-carboxylate, and 5-(trifluoromethyl)benzo[b]thiophene-2-carboxylic acid.

Active Ingredients of Herbicide (1) Phenoxy Fatty Acid Herbicidal Compounds 2,4-PA, MCP, MCPB, phenothiol, mecoprop, fluroxypyr, triclopyr, clomeprop, and naproanilide.

(2) Benzoate Herbicidal Compounds 2,3,6-TBA, dicamba, clopyralid, picloram, aminopyralid, quinclorac, quinmerac.

(3) Urea Herbicidal Compounds

Diuron, linuron, chlortoluron, isoproturon, fluometuron, isouron, tebuthiuron, methabenzthiazuron, cumyluron, daimuron, and methyl-daimuron.

(4) Triazine Herbicidal Compounds

Atrazine, ametoryn, cyanazine, simazine, propazine, simetryn, dimethametryn, metribuzin, triaziflam and indaziflam.

(5) Bipyridinium Herbicidal Compounds

Paraquat and diquat.

(6) Hydroxybenzonitrile Herbicidal Compounds

Bromoxynil and ioxynil.

(7) Dinitroaniline Herbicidal Compounds

Pendimethalin, prodiamine, and trifluralin.

(8) Organophosphorus Herbicidal Compounds

Amiprofos-methyl, butamifos, bensulide, piperophos, anilofos, glyphosate, glufosinate, glufosinate-P, and bialaphos.

(9) Carbamate Herbicidal Compounds

Di-allate, tri-allate, EPTC, butylate, benthiocarb, esprocarb, molinate, dimepiperate, swep, chlorpropham, phenmedipham, phenisopham, pyributicarb, and asulam.

(10) Acid Amide Herbicidal Compounds

Propanil, propyzamide, bromobutide, and etobenzanid.

(11) Chloroacetanilide Herbicidal Compounds

Acetochlor, alachlor, butachlor, dimethenamid, propachlor, metazachlor, metolachlor, pretilachlor, thenylchlor, and pethoxamid.

(12) Diphenyl Ether Herbicidal Compounds

Acifluorfen-sodium, bifenox, oxyfluorfen, lactofen, fomesafen, chlomethoxynil, and aclonifen.

(13) Cyclic Imide Herbicidal Compounds

Oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds

Benzofenap, pyrazolate, pyrazoxyfen, topramezone, and pyrasulfotole

(15) Triketone Herbicidal Compounds

Isoxaflutole, benzobicyclon, sulcotrione, mesotrione, tembotrione, and tefuryltrione.

16) Aryloxyphenoxypropionate Herbicidal Compounds

Clodinafop-propargyl, cyhalofop-butyl, diclofop-methyl, fenoxaprop-ethyl, fluazifop-butyl, haloxyfop-methyl, and quizalofop-ethyl, and metamifop.

(17) Trione Oxime Herbicidal Compounds

Alloxydim-sodium, sethoxydim, butroxydim, clethodim, cloproxydim, cycloxydim, tepraloxydim, tralkoxydim, and profoxydim.

(18) Sulfonyl Urea Herbicidal Compounds

Chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimulfuron, ethoxysulfuron, oxasulfuron-methyl, trifloxysulfuron, foramsulfuron, mesosulfuron-methyl, trifloxysulfuron, tritosulfuron, orthosulfamuron, flucetosulfuron, and propyrisulfuron.

(19) Imidazolinone Herbicidal Compounds

Imazamethabenz-methyl, imazamethapyr, imazamox, imazapyr, imazaquin, and imazethapyr.

(20) Sulfonamide Herbicidal Compounds

Flumetsulam, metosulam, diclosulam, florasulam, cloransulam-methyl, penoxsulam, and pyroxsulam.

(21) Pyrimidinyloxybenzoate Herbicidal Compounds

Pyrithiobac-sodium, bispyribac-sodium, pyriminobac-methyl, pyribenzoxim, pyriftalid, and pyrimisulfan.

(22) Other Herbicidal Compounds

Bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mfenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.

Active Ingredients of Synergist

Piperonyl butoxide, sesamex, sulfoxide, N-(2-ethylhexyl)-8,9,10-trinorborn-5-ene-2,3-dicarboximide (MGK 264), N-declyimidazole), WARF-antiresistant, TBPT, TPP, IBP, PSCP, methyl iodide ($CH_3I$), t-phenylbutenone, diethylmaleate, DMC, FDMC, ETP, and ETN.

EXAMPLES

Hereinbelow, the present invention will be further described in detail by production examples, formulation examples, test examples, and the like. However, the present invention is not limited to these examples.

First, production examples of the compound of the present invention are shown below. In the present invention, TMS represents tetramethylsilane.

Production Example 1

(Tetrahydrofuran-3yl)methylamine hydrochloride (240 mg) and a 1 mol/L aqueous sodium hydroxide solution (5 mL) were simultaneously added to a solution of 5-(1-naphthyloxymethyl)pyridine-2-carboxylic acid chloride (<0.68 mmol) in toluene (10 mL) obtained in Reference Production Example 4, and the mixture was vigorously stirred at room temperature for 20 minutes, and then extracted with ethyl acetate. The organic layer was sequentially washed with 1 mol/L hydrochloric acid and a saturated saline solution, then dried over sodium sulfate, and concentrated under reduced pressure conditions. The residue was applied to a silica gel column chromatography to obtain 208 mg of N-(tetrahydrofuran-3-ylmethyl)-5-(1-naphthyloxymethyl)pyridine -2-carboxylic acid amide (hereinafter, referred to as Compound of the Present Invention (1).) represented by the following formula.

(1)

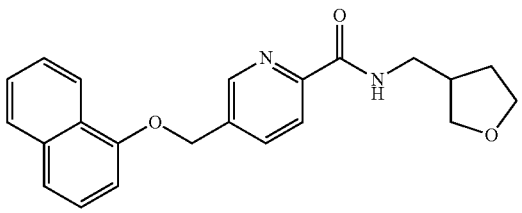

Compound of the Present Invention (1)
$^1$H-NMR (CDCl$_3$, TMS) δ (ppm) : 1.68-1.78 (m, 1H), 2.06-2.16 (m, 1H), 2.59-2.68 (m, 1H), 3.50-3.55 (m, 2H), 3.61-3.67 (m, 1H), 3.75-3.82 (m, 1H), 3.87-3.96 (m, 2H), 5.35 (s, 2H), 6.87-6.91 (m, 1H), 7.36-7.41 (m, 1H), 7.48-7.55 (m, 3H), 7.81-7.85 (m, 1H), 8.02-8.05 (m, 1H), 8.21 (br s, 1H), 8.25-8.32 (m, 2H), 8.72-8.75 (m, 1H).

Production Example 2

A reaction was carried out in the same manner using a solution of unpurified 5-(2-naphthylmethoxymethyl)pyridine-2-carboxylic acid chloride (<0.89 mmol) in toluene (10 mL) obtained in Reference Production Example 6, in place of 5-(1-naphthyloxymethyl)pyridine-2-carboxylic acid chloride (<0.68 mmol) in Production Example 1 to obtain 232 mg of N-(tetranydrofuran-3-ylmethyl)-5-(2-naphthylmethoxymethyl) pyridine-2-carboxylic acid amide (hereinafter, referred to as Compound of the Present Invention (2).) represented by the following formula.

(2)

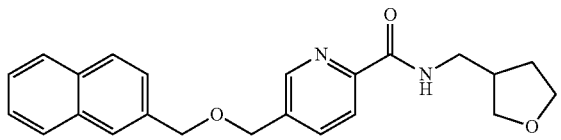

Compound of the Present Invention (2)
$^1$H-NMR (CDCl$_3$, TMS) δ (ppm) : 1.66-1.78 (m, 1H), 2.04-2.19 (m, 1H), 2.55-2.70 (m, 1H), 3.46-3.66 (m, 3H), 3.74-3.82 (m, 1H), 3.86-3.98 (m, 2H), 4.66 (s, 2H), 4.78 (s, 2H), 7.46-7.53 (m, 3H), 7.79-7.95 (m, 5H), 8.16-8.21 (m, 2H), 8.52-8.56 (m, 1H).

Production Example 3

A reaction was carried out in the same manner using a solution of 5-(2-naphthyloxymethyl)pyridine-2-carboxylic acid chloride (<0.57 mmol) in toluene (10 mL) obtained in Reference Production Example 9, in place of 5-(1-naphthyloxymethyl)pyridine-2-carboxylic acid chloride (<0.68 mmol) in Production Example 1 to obtain 214 mg of N-(tetrahydrofuran-3-ylmethyl) -5-(2-naphthyloxymethyl) pyridine -2-carboxylic acid amide (hereinafter, referred to as Compound of the Present Invention (3).) represented by the following formula.

(3)

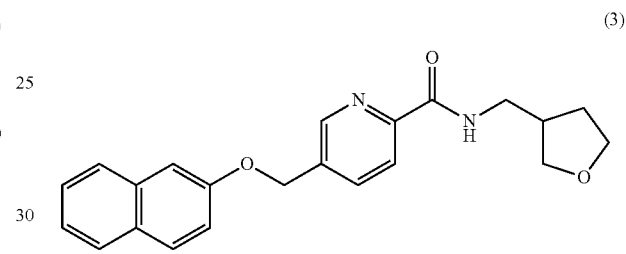

Compound of the Present Invention (3)
$^1$H-NMR (CDCl$_3$, TMS) δ (ppm) : 1.67-1.77 (m, 1H), 2.04-2.15 (m, 1H), 2.58-2.67 (m, 1H), 3.49-3.56 (m, 2H), 3.62 (dd, J=8.9, 5.5 Hz, 1H), 3.74-3.81 (m, 1H), 3.87-3.96 (m, 2H), 5.28 (s, 2H), 7.21-7.25 (m, 2H), 7.35-7.40 (m, 1H), 7.44-7.49 (m, 1H), 7.72-7.81 (m, 3H), 7.98-8.02 (m, 1H), 8.20 (br s, 1H), 8.23-8.26 (m, 1H), 8.67-8.69 (m, 1H).

Production Example 4

A reaction was carried out in the same manner using a solution of unpurified 3-fluoro-5-(2-naphthylmethoxymethyl)pyridine-2-carboxylic acid chloride (<1.94 mmol) in toluene (15 mL) obtained in Reference Production Example 12, in place of 5-(1-naphthyloxymethyl) pyridine-2-carboxylic acid chloride (<0.68 mmol) in Production Example 1 to obtain 100 mg of 3-fluoro-5-(2-naphthylmethoxymethyl)-pyridine-2-carboxylic acid amide (hereinafter, referred to as Compound of the Present Invention (4).) represented by the following formula.

(4)

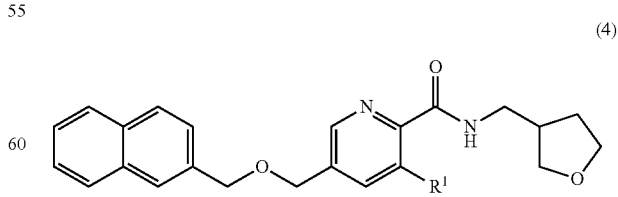

Compound of the Present Invention (4)
$^1$H-NMR (CDCl$_3$, TMS) δ (ppm) : 1.64-1.77 (m, 1H), 2.03-2.13 (m, 1H), 2.55-2.67 (m, 1H), 3.41-3.55 (m, 2H), 3.61 (dd, J=8.8, 5.4 Hz, 1H), 3.73-3.80 (m, 1H), 3.85-3.95

(m, 2H), 4.65 (s, 2H), 4.79 (s, 2H), 7.47-7.53 (m, 3H), 7.57-7.62 (m, 1H), 7.79-7.89 (m, 4H), 7.98 (br s, 1H), 8.33-8.34 (m, 1H).

Production Example 5

5-[2-(1-Naphthyloxy)ethyl]pyridine-2-carboxylic acid sodium salt (300 mg, 0.95 mmol) obtained in Reference Production Example 14, (tetrahydrofuran-3-yl)methylamine hydrochloride (176 mg, 1.25 mmol) and 1-hydroxybenzotriazole (14 mg, 0.10 mmol) were added to chloroform (6 mL), and triethylamine (0.29 mL, 2.05 mmol) was further added, then 1-ethyl-3-(3-dimethylaminopropyl) carbodiimide hydrochloride (225 mg, 1.18 mmol) was added, and the mixture was stirred at room temperature or 4 hours, and concentrated under reduced pressure conditions. The residue was applied to a silica gel column chromatography to obtain 319 mg of N-(tetrahydrofuran-3-ylmethyl)-5-[2-(1-naphthyloxy)ethyl]pyridine -2-carboxylic acid amide (hereinafter, referred to as Compound of the Present Invention (5).) represented by the following formula.

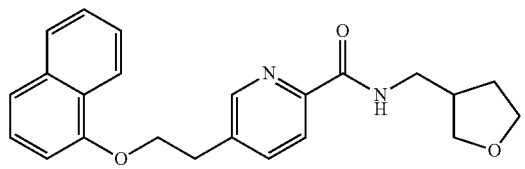

(5)

Compound of the Present Invention (5)
$^1$H-NMR (CDCl$_3$, TMS) δ (ppm) : 1.66-1.76 (m, 1H), 2.03-2.14 (m, 1H), 2.56-2.65 (m, 1H), 3.29-3.35 (m, 2H), 3.47-3.54 (m, 2H), 3.58-3.64 (m, 1H ), 3.73-3.81 (m, 1H), 3.85-3.95 (m, 2H), 4.38-4.43 (m, 2H), 6.78-6.81 (m, 1H), 7.35-7.37 (m, 1H), 7.41-7.51 (m, 2H), 7.77-7.39 (m, 3H) , 8.13-3.22 (m, 3H), 8.57-8.60 (m, 1H).

Production Example 6

A reaction was carried out in the same manner using 5-[2-(2-naphthyloxy)ethyl]pyridine-2-carboxylic acid sodium salt (300 mg, 0.95 mmol) obtained in Reference Production Example 16, in place of 5-[2-(1-naphthyloxy)ethyl]pyridine-2-carboxylic acid sodium salt (300 mg, 0.95 mmol) in Production Example 5 to obtain 80 mg of N-(tetrahydrofuran-3-ylmethyl)-5-[2-naphthyloxy)ethyl]pyridine -2-carboxylic acid amide (hereinafter, referred to as Compound of the Present Invention (6).) represented by the following formula.

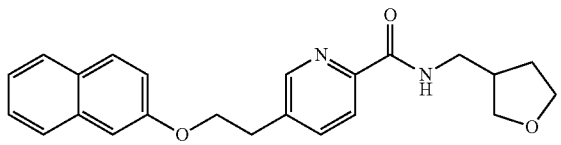

(6)

Compound of the Present Invention (6)
$^1$-NMR (CDCl$_3$, TMS) δ (ppm) : 1.66-1.76 (m, 1H), 2.03-2.14 (m, 1H), 2.56-2.67 (m, 1H), 3.21-3.25 (m, 2H), 3.47-3.54 (m, 2H), 3.59-3.64 (m, 1H), 3.74-3.81 (m, 1H), 3.86-3.95 (m, 2H), 4.31-4.36 (m, 2H), 7.10-7.14 (m, 2H), 7.32-7.37 (m, 1H), 7.41-7.46 (m, 1H), 7.69-7.85 (m, 4H), 8.14-8.20 (m, 2H), 8.52-8.54 (m, 1H).

Next, reference production examples of an intermediate used in the production of the compound of the present invention are shown.

Reference Production Example 1

Triethylamine (0.54 mL, 3.89 mmol) was added to a solution of methyl 5-hydroxymethylpyridine-2-carboxylate (0.50 g, 2.99 mmol) in chloroform (12 ml). Methanesulfonyl chloride (0.30 mL, 3.89 mmol) was slowly added dropwise under ice-water cooling, and the mixture was stirred for 20 minutes. Thereafter, water was added, and the mixture was extracted three times with ethyl acetate. The organic layer was washed with a saturated saline solution, then dried over sodium sulfate, and concentrated under reduced pressure conditions. The residue was suspended in a mixed solution of diisopropyl ether and hexane, and the precipitate was filtered to obtain 643 mg of methyl 5-methanesulfonyloxymethylpyridine-2-carboxylate represented by the following formula.

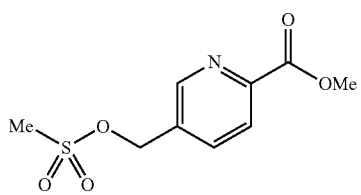 [SMILES: COC(=O)c1ccc(COS(C)(=O)=O)cn1]

$^1$H-NMR (CDCl$_3$, TMS) δ (ppm) : 3.06 (s, 3H), 4.04 (s, 3H), 5.34 (s, 2H), 7.94 (dd, J=8.1, 2.1 Hz, 1H), 8.20 (d, J32 8.1 Hz, 1H), 8.77 (d, J=2.1 Hz, 1H).

Reference Production Example 2

Potassium carbonate (293 mg, 2.12 mmol) and 1-naphthol (306 mg, 2.12 mmol) were added to a solution of methyl 5-methanesulfonyloxymethylpyridine-2-carboxylate (260 mg, 1.06 mmol) in tetrahydrofuran (10 mL), and the mixture was stirred at a range of 50 to 60° C. for 2 hours. After cooling, the mixture was concentrated under reduced pressure conditions, then water was added to the concentrate, and the mixture was extracted with ethyl acetate. The organic layer was washed with a saturated saline solution, then dried over sodium sulfate, and concentrated under reduced pressure conditions. The residue was applied to a silica gel column chromatography to obtain 210 mg of methyl 5-(1-naphthyloxymethyl)pyridine-2-carboxylate represented by the following formula.

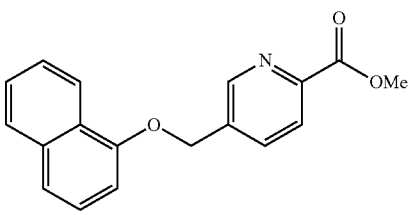 [SMILES: COC(=O)c1ccc(COc2cccc3ccccc23)cn1]

$^1$H-NMR (CDCl$_3$, TMS) δ (ppm) : 4.04 (s, 3H), 5.37 (s, 2H), 6.86-6.90 (m, 1H), 7.35-7.41 (m, 1H), 7.48-7.55 (m, 3H), 7.81-7.85 (m, 1H), 8.04-8.08 (m, 1H), 8.20-8.22 (m, 1H), 8.29 (d, J=15.5 Hz, 1H) 8.91-8.93 (m, 1H).

Reference Production Example 3

A 1 mol/L aqueous sodium hydroxide solution (5 ml) was added to a solution of methyl 5-(1-naphthyloxymethyl)pyridine-2-carboxylate (210 mg, 0.72 mmol) in tetrahydrofuran (5 mL), and the mixture was vigorously stirred at room temperature 15 minutes, and then, after adjusting the pH to 3 to 4 by adding 1 mol/L, extracted with ethyl acetate. The organic layer was washed with a saturated saline solution, then dried over sodium sulfate, and concentrated under reduced pressure conditions to obtain 5-naphthyloxymethyl)pyridine-2-carboxylic acid represented by the following formula,

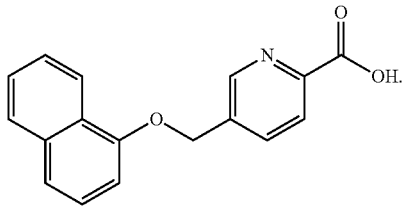 [SMILES: O=C(O)c1ccc(COc2cccc3ccccc23)cn1]

The product was subjected to a next reaction without purification.

$^1$H-NMR (CDCl$_3$, TMS) δ (ppm) : 5.40 (s, 2H), 6.88 (d, J=7.7 Hz, 1H), 7.36-7.42 (m, 1H), 7.49-7.57 (m, 3H), 7.83-7.86 (m, 1H), 8.13-8.17 (m, 1H), 8.28-8.33 (m, 2H), 8.81-8.83 (m, 1H).

Reference Production Example 4

N,N-Dimethylformamide (about 0.05 mL) and oxalyl chloride (about 0.15 mL) were added to a solution of 5-(1-naphthyloxymethyl)pyridine-2-carboxylic acid (190 mg, <0.68 mmol) in ethyl acetate (20 mL) obtained in Reference Production Example 3, then the mixture was stirred at room temperature for 15 minutes and concentrated under reduced pressure conditions, and then toluene (about 10 mL) was added to obtain 5-(1-naphthyloxymethyl)pyridine-2-carboxylic acid chloride represented by the following formula as a toluene solution (<0.68 mmol),

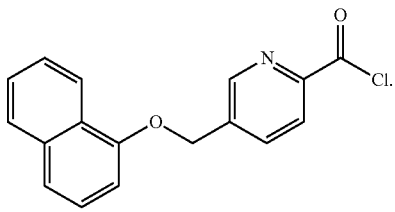 [SMILES: O=C(Cl)c1ccc(COc2cccc3ccccc23)cn1]

The product was used in Production Example 1 without purification.

Reference Production Example 5

Potassium-tert-butoxide (824 mg, 7.34 mmol) was added to a solution of 2-naphthalenemethanol (1.16 g, 7.34 mmol) in tetrahydrofuran (25 mL), and methyl 5-methanesulfonyloxymethylpyridine-2-carboxylate (600 mg, 2.45 mmol) was added while stirring the mixture. The mixture was stirred at 45 to 55° C. for 2 hours and then concentrated under reduced pressure conditions. Water was added to the concentrate, and the mixture was washed with ethyl acetate. The pH of the aqueous layer was adjusted to 2 to 3 with a 1.5% hydrochloric acid, and then the mixture was saturated with sodium chloride and extracted twice with ethyl acetate. The organic layer was dried over sodium sulfate and then concentrated under reduced pressure to obtain 520 mg of 5-(2-naphthylmethoxymethyl)pyridine-2-carboxylic acid represented by the following formula as a mixture,

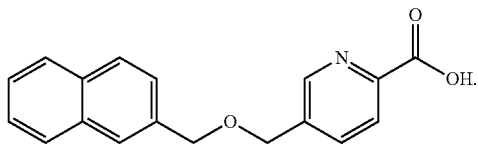 [SMILES: O=C(O)c1ccc(COCc2ccc3ccccc3c2)cn1]

The product was subjected to a next reaction without purification.

Reference Production Example 6

DMF (about 0.1 mL) and oxalyl chloride (about 0.3 mL) were added to a solution of unpurified 5-(2-naphthylmethoxymethyl)pyridine-2-carboxylic acid (260 mg, <0.89 mmol) in ethyl acetate (20 mL) obtained in Reference Production Example 5, and then the mixture was stirred at room temperature for 10 minutes and concentrated under reduced pressure conditions. Toluene (about 10 mL) was added to the concentrate to obtain 5-(2-naphthylmethoxymethyl)pyridine-2-carboxylic acid chloride represented by the following formula as a toluene solutions (<0.89 mmol),

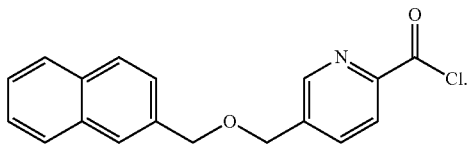 [SMILES: O=C(Cl)c1ccc(COCc2ccc3ccccc3c2)cn1]

The product was used in Production Example 2 without purification.

Reference Production Example 7

2-Naphthol (306 mg, 2.12 mmol) and potassium carbonate (293 mg, 2.12 mmol) were added to a solution of methyl 5-methanesulfonyloxymethylpyridine-2-carboxylate (260 mg, 1.06 mmol) in tetrahydrofuran (10 mL), and the mixture was stirred at 50 to 60° C. for 2 hours and cooled, then concentrated under reduced pressure conditions. Water was added to the concentrate, and the mixture was extracted with ethyl acetate. The organic layer was washed with a saturated saline solution, then dried over sodium sulfate, and concentrated under reduced pressure conditions. The residue was applied to a silica gel column chromatography to obtain 180 mg of methyl 5-(2naphthyloxymethyl)pyridine-2-carboxylate represented by the following formula.

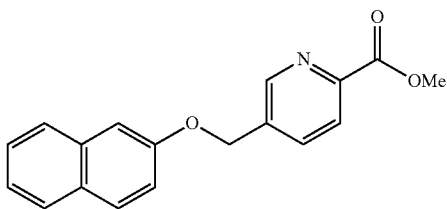 [SMILES: COC(=O)c1ccc(COc2ccc3ccccc3c2)cn1]

¹H-NMR (CDCl₃, TMS) δ (ppm) : 4.03 (s, 3H), 5.30 (s, 2H), 7.20-7.25 (m, 2H), 7.35-7.40 (m, 1H), 7.44-7.49 (m, 1H), 7.71-7.75 (m, 1H), 7.79 (d, J=8.7 Hz, 2H), 8.00-8.03 (m, 1H), 8.18-8.21 (m, 1H), 8.85-8.88 (m, 1H).

Reference Production Example 8

A 1 mol/L aqueous sodium hydroxide solution (5 mL) was added to a solution of methyl 5-(2-naphthyloxymethyl)pyridine-2-carboxylate (180 mg, 0.61 mmol) in tetrahydrofuran (5 mL), and the mixture was stirred at room temperature for 1 hour, and after adjusting the pH to 2 to 3 by adding 1 mol/L hydrochloric acid, extracted with ethyl acetate. The organic layer was washed with a saturated saline solution, then dried over sodium sulfate, and concentrated under reduced pressure conditions to obtain 160 mg of 5-(2-naphthyloxymethyl)pyridine-2-carboxylic acid represented by the following formula,

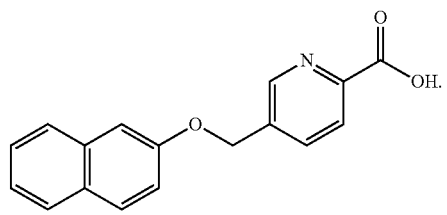 [SMILES: O=C(O)c1ccc(COc2ccc3ccccc3c2)cn1]

The product was subjected to a next reaction without purification.

¹H-NMR (CDCl₃, TMS) δ (ppm):5.33 (s, 2H), 7.21-7.26 (m, 2H) 7.36-7.41.(m, 1H), 7.45-7.50 (m, 1H), 7.72-7.76 (m, 1H), 7.79-7.82 (m, 2H), 8.08-8.12 (m, 1H), 8.27-8.30 (m, 1H), 8.76-8.77 (m, 1H).

Reference Production Example 9

N,N-Dimethylformamide (about 10 mg) and oxalyl chloride (about 0.25 g) were added to a solution of 5-(2-naphthyloxymethyl)pyridine-2-carboxylic acid (160 mg, <0.57 mmol) in ethyl acetate (30 mL) obtained in Reference Production Example 8, and then the mixture was stirred at room temperature for 15 minutes and concentrated under reduced pressure conditions. Toluene (about 10 mL) was added to the concentrate to obtain 5-(2-naphthyloxymethyl)pyridine-2-carboxylic acid chloride represented by the following formula as a toluene solution (<0.57 mmol),

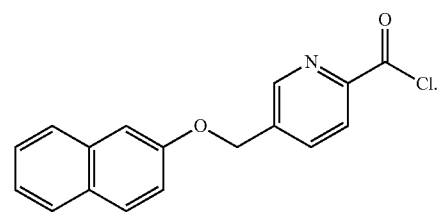 [SMILES: O=C(Cl)c1ccc(COc2ccc3ccccc3c2)cn1]

The product was used in Production Example 3 without purification.

Reference Production Example 10

2-Naphthylmethyl (1.70 g, 15.7 mmol) was added to a solution of 3-fluoro-5-methanesulfonyloxymethylpyridine (806 mg, 3.93 mmol) in tetrahydrofuran (5 mL) and dimethyl sulfoxide (8 mL). Potassium-tert-butoxide (1.76 g, 15.7 mmol) was added under ice cooling, and the mixture was stirred at a range of 5° C. to room temperature for 1 hour and diluted with ethyl acetate and hexane, and then sequentially washed with water and a saturated saline solution. The organic layer was dried over sodium sulfate and then concentrated under reduced pressure conditions, and the residue was applied to a silica gel column chromatography to obtain 803 mg of 3-fluoro-5-(2-naphthylmethoxymethyl)pyridine represented by the following formula.

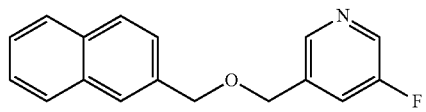 [SMILES: Fc1cncc(COCc2ccc3ccccc3c2)c1]

¹H-NMR (CDCl₃, TMS) δ (ppm) : 4.62 (s, 2H), 4.77 (s, 2H), 7.46-7.52 (m, 4H), 7.80-7.89 (m, 4H) , 8.40-8.43 (m, 2H).

Reference Production Example 11

A 1.64 mol/L-n-butyllithium hexane solution (3.65 mL, 5.99 mmol) was added dropwise to a solution of 2-bromo-1,3,5-trimethylbenzene (1.19 g, 5.99 mmol) in tetrahydrofuran (20 mL) at −65° C. or lower in a nitrogen atmosphere, and the mixture was stirred at −65° C. or lower for 1 hour. Thereafter, a solution of 3-fluoro-5-(2-naphthylmethoxymethyl)pyridine (800 mg, 2.99 mmol) in tetrahydrofuran (5 mL) was added, and the mixture was stirred at a range of −65 to −60° C. for 1 hour. Carbon dioxide was added to the reaction solution under cooling, and the mixture was stirred at a range form −65° C. to 10° C. for 2 hours, then concentrated under reduced pressure conditions, diluted with ethyl acetate, and then extracted with water. The pH of the aqueous layer was adjusted to 2 to 3 by adding dilute hydrochloric acid, then sodium chloride was added, and the mixture was extracted twice with ethyl acetate. The ethyl acetate layers were combined and dried over sodium sulfate, and then concentrated under reduced pressure conditions. The residue was applied to a silica gel column chromatography to obtain 6.03 mg of 3-fluoro-5-(2-naphthylmethoxymethyl)pyridine-2-carboxylic acid represented by the following formula as a crude product,

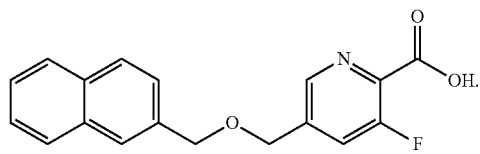 [SMILES: O=C(O)c1ncc(COCc2ccc3ccccc3c2)cc1F]

The product was subjected to a next reaction without purification.

Reference Production Example 12

DMF (about 0.1 mL) and oxalyl chloride (about 1 mL) were added to a solution of unpurified 3-fluoro-5-(2-naphthylmethoxymethyl)pyridine-2-carboxylic acid (6.03 mg, <1.94 mmol) in ethyl acetate (20 mL) obtained in Reference Production Example 11, and then the mixture was stirred at room temperature for 10 minutes and concentrated under reduced pressure conditions. Toluene (about 15 mL) was added to the concentrate to obtain 3-fluoro-5-(2-naphthyl-methoxymethyl)pyridine-2-carboxylic acid chloride as a toluene solution (<1.94 mmol),

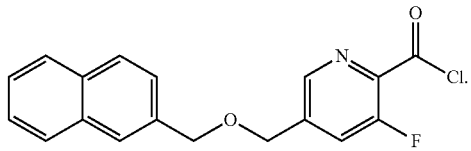 [SMILES: O=C(Cl)c1ncc(COCc2ccc3ccccc3c2)cc1F]

The product was used in Production Example 4 without purification.

Reference Production Example 13

Triphenylphosphine (2.17 g, 8.28 mmol), 1-naphthol (1.19 g, 8.28 mmol) and diisopropyl azodicarboxylate (about 1.9 mol/L toluene solution, 4.4 mL, 8.36 mmol) were added to a solution of methyl 5-(2-hydroxyethyl)pyridine-2-carboxylate (1.00 g, 5.52 mmol) in tetrahydrofuran (50 mL), and the mixture was stirred at room temperature for 3 hours and 30 minutes, and then concentrated under reduced pressure conditions. The residue was applied to a silica gel column chromatography to obtain 900 mg of methyl 5-[2-(1-naphthyloxy)ethyl]pyridine-2-carboxylate represented by the following formula.

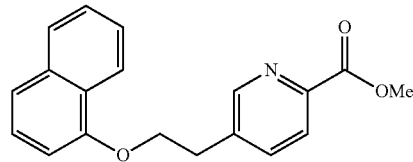

$^1$H-NMR (CDCl$_3$, TMS) δ (ppm) : 3.34(t, J=6.1 Hz, 2H), 4.01 (s, 3H), 4.41 (t, J=6.1 Hz, 2H), 6.77-6.82 (m, 1H), 7.32-7.38 (m, 1H), 7.41-7.52 (m, 3H), 7.76-7.81 (m, 1H), 7.85-7.90 (m, 1H), 8.10-8.19 (m, 2H), 8.79-8.83 (m, 1H).

Reference Production Example 14

A 6 mol/L aqueous sodium hydroxide solution (20 ml) was added to a solution of methyl 5-[2-(1-naphthyloxy)ethyl]pyridine-2-carboxylate (900 mg, 2.93 mmol) in tetrahydrofuran (30 mL) and the mixture was stirred at 50° C. for 5 hours. After cooling to room temperature, water was added, and the precipitate was filtered to obtain 482 mg of 5-[2-(naphthyloxy)ethyl]pyridine-2-carboxylic acid sodium salt represented by the following formula,

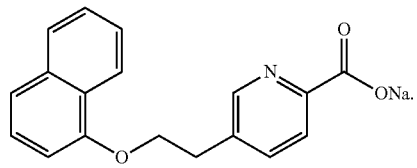

The product was used in Production Example 5 without purification.

$^1$H-NMR (DMSO-d$_6$, TMS) δ (ppm) : 3.31 (t, J=6.1 Hz, 2H), 4.43 (t, J=6.1 Hz, 2H), 6.97-7.01 (m, 1H), 7.37-7.54 (m, 4H), 7.83-7.87 (m, 1H), 8.00-8.09 (m, 3H), 8.77-8.79 (m,1H).

Reference Production Example 15

A reaction was carried out in the same manner using 2-naphthol (1.19 g, 8.28 mmol), in place of 1-naphthol (1.19 g, 8.28 mmol) in Reference Production Example 13 to obtain 860 mg of methyl 5-[2-(2-naphthyloxy)ethyl]pyridine-2-carboxylate represented by the following formula.

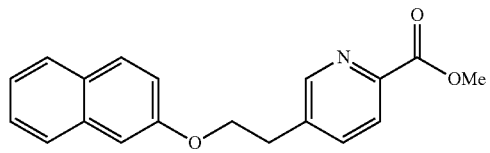 [SMILES: COC(=O)c1ccc(CCOc2ccc3ccccc3c2)cn1]

$^1$H-NMR (CDCl$_3$, TMS) δ (ppm) : 3.25 (t, J=6.3 Hz, 2H), 4.01 (s, 3H), 4.34 (t, J=6.3 Hz, 2H), 7.09-7.13 (m, 2H), 7.32-7.36 (m, 1H), 7.41-7.46 (m, 1H), 7.69-7.78 (m, 3H), 7.81-7.85 (m, 1H), 8.10-8.13 (m, 1H), 8.73-8.74 (m, 1H).

Reference Production Example 16

A reaction was carried out in the same manner using methyl 5-[2-(2-naphthyloxy)ethyl]pyridine-2-carboxylate (860 mg, 2.80 mmol), in place of 5-[2-(1-naphthyloxy)ethyl]pyridine-2-carboxylate (900 mg, 2.93 mmol) in Reference Production Example 14 to obtain 569 mg of 5-[2-(2-naphthyloxy)ethyl]pyridine-2-carboxylic acid sodium salt represented by the following formula,

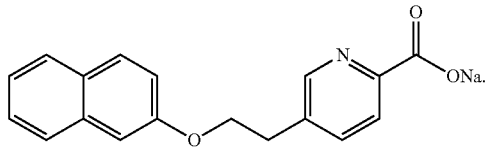

The product was used in Production Example 6 without purification.

$^1$H-NMR (DMSO-d$_6$, TMS) δ (ppm) : 3.25 (t, J=6.3 Hz, 2H), 4.38 (t, J=6.3 Hz, 2H), 7.11-7.16 (m, 1H), 7.31-7.38 (m, 2H), 7.42-7.48 (m, 1H), 7.77-7.84 (m, 3H), 8.04-8.10 (m, 2H), 8.72-8.76 (m, 1H).

Next, speific examples of the compound of the present invention are exemplified below.

Compounds represented by formula (I-A), wherein R$^1$, m and n represent any combination described below.

(I-A)

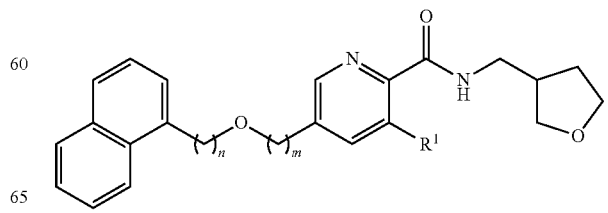

Compounds represented by formula (I-B), wherein $R^1$, m and n represent any combination described below.

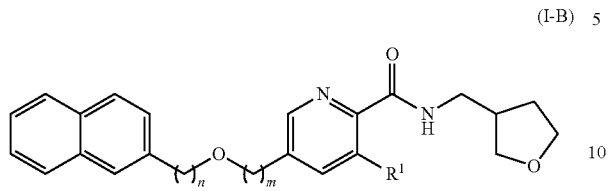

(I-B)

Examples of $R^1$, m and n in the compounds represented by the formula (I-A) and the compounds represented by the formula (I-B) are shown below. Below, branch number, group represented by $R^1$, m and n are listed in order in the bracket. [branch number, $R^1$, m, n]=[1, H, 1, 0], [2, H, 2, 0], [3, H, 1, 1], [4, H, 2, 1], [5, F, 1, 0], [10, Cl, 2, 0], [11, Cl, 1, 1], [8, F, 2, 1, ], [9, Cl, 1, 0], [10, Cl, 2, 0], [11, Cl, 1, 1], [12, Cl, 2, 1], [13, Br, 1, 0[, ]14, Br, 2, 0], [15, Br, 1, 1], [16, Br, 2, 1], [17, I, 1, 0], [18, I, 2, 0], [19, I, 1, 1], [20, I, 2, 1].

Next, formulation examples are shown. Here, the part means part by weight.

Formulation Example 1

Twenty (20) parts of any one of Compounds of the Present Invention (1) to (6) is dissolved in 65 parts xylene, and 15 parts of Sorpol 3005X (a registered trademark of TOHO Chemical Industry Co., Ltd.) is added, and then the mixture is well mixed with stirring to obtain an emulsifiable concentrate.

Formulation Example 2

Five (5) parts of Sorpol 3005X is added to 40 parts of any one of Compounds of the Present Invention (1) to (6), and the mixture is well mixed. Thirty two (32) parts of Carplex #80 (synthetic hydrous silicon oxide, a registered trademark of Shionogi & Co., Ltd.) and 23 parts of 300-mesh diatomaceous earth are added thereto, and the mixture is mixed with stirring with a juice blender to obtain wettable powder.

Formulation Example 3

One and five tenths (1.5) parts of any one of Compounds of the Present Invention (1) to (6) and 1 part of Tokuseal GUN (synthetic hydrous silicon oxide, manufactured by Tokuyama Corporation), 2 parts of Reax 85A (sodium lignin sulfonate, manufactured by West Vaco Chemicals), 30 parts of Bentonite Fuji (bentonite, manufactured by HOJUN., Co., Ltd.) and 65.5 parts of Shokozan A clay (kaolin clay, manufactured by SHOKOZAN MINING Co., Ltd.) are well pulverized, and water is added thereto. The mixture is well kneaded, then granulated by an extrusion granulator, and dried to obtain 1.5% granules.

Formulation Example 4

Ten (10) parts of any one of Compounds of the Present Invention (1) to (6), 10 parts of phenylxylylethane and 0.5 parts of SUMIDUR L-75 (tolylene diisocyanate, manufactured by Sumika Bayer Urethane Co., Ltd.) are mixed, and then added to 20 parts of a 10% aqueous solution of gum arabic, and the mixture is stirred with a homomixer to obtain an emulsion with an average particle size of 20 μm. Two (2) parts of ethylene glycol is added thereto, and the mixture is further stirred in a warm bath at a temperature of 60° C. for 24 hours to obtain microcapsule slurry. On the other hand, 0.2 parts of xanthan gum and 1.0 part of VEEGUM R (aluminum magnesium silicate, a registered trademark, Vanderbilt Company, Inc.) are dispersed in 56.3 parts of ion-exchanged water to obtain a thickener solution. Then, 42.5 parts of the microcapsule slurry and 57.5 parts of the thickener solution are mixed to obtain a microcapsule formulation.

Formulation Example 5

Ten (10) parts of any one of Compounds of the Present Invention (1) to (6) and 10 parts of phenylxylylethane are mixed and then added to 20 parts of a 10% aqueous solution of polyethylene glycol, and the mixture is stirred with a homomixer to obtain an emulsion with an average particle size of 3 μm. On the other hand, 0.2 part of xanthan gum and 1.0 part of VEEGUM R. (aluminum magnesium silicate, a registered trademark, Vanderbilt Company, Inc) are dispersed 58.8 parts of ion-exchanged water to obtain a thickener solution. Then, 40 parts of the emulsion solution and 60 parts of the thickener solution are mixed to obtain a flowable.

Formulation Example 6

Three (3) parts of Carplex #80 (synthetic hydrous silicon oxide fine powder, a registered trademark of Shionogi & Co., Ltd.), 0.3 parts of PAP (a mixture of monoisopropyl phosphate and diisopropyl phosphate) and 91.7 parts of talc (300 mesh) are added to 5 parts of any one of Compounds of the Present Invention (1) to (6), and the mixture is mixed with stirring with a juice blender to obtain a dust formulation.

Formulation Example 7

One tenth (0.1) parts of any one of Compounds of the Present Invention (1) to (6) is dissolved in 10 parts of isopropyl alcohol, and the solution is mixed with 89.9 parts of deodorized kerosene to obtain an oil formulation.

Formulation Example 8

One (1) part of any one of Compounds of the Present Invention (1) to (6), 5 parts of dichloromethane and 34 parts of deodorized kerosene are mixed and dissolved, and filled into an aerosol container, and a valve portion is installed. Then, 60 parts of power propellant (liquefied petroleum gas) is filled therein under pressure through the valve portion to obtain an oil-based aerosol.

Formulation Example 9

A mixed solution of 0.6 parts of any one of Compounds of the Present invention (1) to (6), 5 parts of xylene, 3.4 parts of deodorized kerosene and 1 part of ATGMOS 300 (emulsifier, a registered trademark of Atlas Chemical, Inc.) and 50 parts of water are filled into an aerosol container, and 40 parts of power propellant (liquified petroleum gas) are filled therein under pressure through the valve portion to obtain an aqueous aerosol.

Formulation Example 10

Three tenths (0.3) g of any one of Compounds of the Present Invention (1) to (6) is dissolved in 20 ml of acetone, and the solution is uniformly mixed with stirring with 99.7 g of a base material for an incense stick (obtaining by mixing tabu powder, pyrethrum marc and wooden powder at a ratio of 4:3:3). Then, 100 ml of water is added thereto, and the mixture is thouroughly kneaded, molded and dried to obtain an insecticidal coil.

Formulation Example 11

Eight tenths (0. 8) g of any one of Compounds of the Present Invention (1) to (6) and 0.4 g piperonyl butoxide is dissolved by adding acetone, and the total volume is adjusted to 10 ml with acetone. Then, 0.5 ml of this solution is uniformly impregnated into a base material for an electric insecticidal mat (a plate obtained by hardening fibrils of a mixture of cotton linters and pulp) with a size of 2.5 cm×1.5 cm and a thickness of 0.3 cm to obtain an electric insecticidal mat formulation.

Formulation Example 12

Three (3) parts of any one of Compounds of the Present Invention (1) to (6) is dissolved in 97 parts of deodorized kerosene to obtain a liquid formulation, and this is poured into a vessel made of vinyl chloride. A liquid absorptive core whose upper part can be heated by a heater (an inorganic powder is hardened with a binder and sintered) is inserted thereinto to obtain a part to be used for a liquid absorptive core type thermal transpiration apparatus.

Formulation Example 13

One hundred (100) mg of any one of Compounds of the Present Invention (1) to (6) is dissolved in an appropriate amount of acetone, and the solution is impregnated in a porous ceramic plate with a size of 4.0×4.0 cm and 1.2 cm in thickness to obtain a heating type smoking agent.

Formulation Example 14

One hundred (100) μg of any one of Compounds of the Present Invention (1) to (6) is dissolved in an appropriate amount of acetone, and the solution is uniformly applied to a filter paper with a size of 2 cm×2 cm and a thickness of 0.3 mm and then air-dried to remove acetone. A normal temperature volatile agent was obtained.

Formulation Example 15

Ten (10) parts of any one of Compounds of the Present Invention (1) to (6), 35 parts of white carbon containing 50 parts of polyoxvethylene alkyl ether sulfate ammnonium salt and 55 parts of water are mixed and finely pulverized by a wet pulverization method to obtain a formulation.

Next, the arthropod pest control effect of the compound of the present invention is shown as test examples.

Test Example 1

The oil formulations of Compounds of the Present Invention (1), (2) and (4) to (6) obtained in Formulation Example 7 were diluted with a mixed solution of isopropyl alcohol/deodorized kerosene=1/9 so as to have a concentration of the active ingredient of 2.0% w/v to prepare a test drug solution.

Ten Blattella germanica (5 males and 5 females) were released in a test container (8.75 cm in diameter, 7.5 cm in height, and the bottom made of 16 mesh metallic wire) with the inner wall on which butter was applied, and the container was placed on the bottom of a test chamber (bottom: 46 cm×46 cm, height: 70 cm). From a height of 60 cm above the upper surface of the container, 1.5 of the test drug solution was sprayed using a spray gun (a spraying pressure of 0.42 kg/cm$^2$). Thirty seconds after spraying, the container was taken out from the test chamber, and after 2 minutes, 5 minutes and 15 minutes, the number of knockdown insects was counted to obtain a knockdown rate. The knockdown rate was calculated by the following equation.

Knockdown Rate (%)=(Number of Knockdown Insects/Number of Tested Insects)×100

As a result, in treatments with Compounds of the Present Invention (1), (2) and (4) to (6), the knockdown rate of the tested insects within 15 minutes was 80% or more.

Test Example 2

The oil formulation of Compounds of the Present Invention (2) and (5) obtained in Formulation Example 7 were diluted with a mixed solution of isopropyl alcohol/deodorized kerosene=1/9 so as to have at concentration of the active ingredient of 2.0% w/v and a test drug solution was prepared.

Ten adult Musca domestica (five males and five females) were released in a polyethylene cup (bottom diameter: 10.6 cm), and the cup was covered with a 16-mesh nylon gauze. The polyethylene cup was placed on the bottom of a test chamber (bottom: 46 cm×46 cm, height: 70 cm). From a height of 30 cm above the upper surface of the polyethylene cup, 0.5 ml of the test drug solution was sprayed using a spray gun (a spraying pressure of 0.9 kg/cm$^2$). Immediately after spraying, the cup was taken out from the test chamber, and after 2 minutes, 5 minutes and 15 minutes, the number of knockdown insects was counted to obtain a knockdown rate. The knonkdown rate was calculated by the following equation.

Knockdown Rate (%)=(Number of Knockdown Insects/Number of Tested Insects)×100

As a result, in treatments with Compounds of the Present Invention (2) and (5), the knockdown rate of the tested insects within 15 minutes was 80% or more.

Test Example 3

The oil formulations of Compounds of the Present Invention (1) to (6) obtained in Formulation Example 7 were diluted with a mixed solution of isopropyl alcohol/deodorized kerosene=1/9 so as to have a concentration of the active ingredient of 0.1% w/v and a test drug solution was prepared.

Ten adult Culex pipens pallens were released in a polyethylene cup (bottom diameter: 10.6 cm), and the cup was covered with a 16-mesh nylon gauze. The polyethylene cup was placed on the bottom of a test chamber (bottom: 46 cm×46 cm, height: 70 cm). From a height of 30 cm above the upper surface of the polyethylene cup, 0.5 ml of the test drug solution was sprayed using a spray gun (a spraying pressure of 0.4 kg/cm$^2$). Immediately after spraying, the cup was taken out from the test chamber, and after 2 minutes, 5 minutes and 15 minutes, the number of knockdown insects was counted to obtain a knockdown rate. The knockdown rate was calculated by the following equation.

Knockdown Rate (%)=(Number of Knockdown Insects/Number of Tested Insects)×100

As a result, in treatments with Compounds of the Present Invention (1) to (6), the knockdown rate of the tested insects within 15 minutes was 80% or more.

The compound of the present invention has a controlling effect on arthropod pests and is useful as an active ingredient of an arthropod pest control agent.

What is claimed is:

1. An amide compound represented by formula (I),

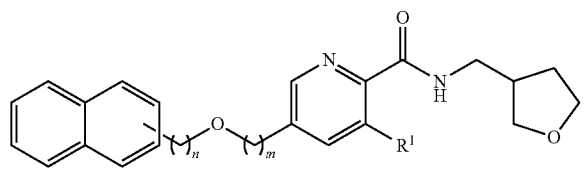

wherein
$R^1$ represents a hydrogen atom or a halogen atom,
m represents 1 or 2, and
n represents 0 or 1.

2. The amide compound according to claim 1, wherein $R^1$ is a hydrogen atom or a fluorine atom.

3. An arthropod pest control agent comprising the amide compound as defined in claim 1, and an inert carrier.

4. A method for controlling arthropod pests comprising a step of applying an effective amount of the amide compound as defined in claim 1 to an arthropod pest or an arthropod pest-infested area.

5. An arthropod pest control agent comprising the amide compound as defined in claim 2, and an inert carrier.

6. A method for controlling arthropod pests comprising a step of applying an effective amount of the amide compound as defined in claim 2 to an arthropod pest or an arthropod pest-infested area.

* * * * *